United States Patent
Huang et al.

(10) Patent No.: US 9,630,927 B2
(45) Date of Patent: Apr. 25, 2017

(54) METHOD AND MANUFACTURING SYSTEM

(71) Applicant: Taiwan Semiconductor Manufacturing Company Limited, Hsinchu (TW)

(72) Inventors: Wei-Pin Huang, Miaoli County (TW); Wen-Chi Chien, Miaoli County (TW); Bing-Yuan Cheng, Hsinchu County (TW); Feng-Ning Lee, Taoyuan County (TW); Wei-Cheng Wang, Taoyuan County (TW)

(73) Assignee: Taiwan Semiconductor Manufacturing Company Limited, Hsinchu (TW)

( * ) Notice: Subject to any disclaimer, the term of this patent is extended or adjusted under 35 U.S.C. 154(b) by 450 days.

(21) Appl. No.: 14/157,567

(22) Filed: Jan. 17, 2014

(65) Prior Publication Data

US 2015/0206734 A1    Jul. 23, 2015

(51) Int. Cl.
*G01N 21/88* (2006.01)
*G01N 21/63* (2006.01)
(Continued)

(52) U.S. Cl.
CPC ......... *C07D 237/32* (2013.01); *C07D 401/10* (2013.01); *C07D 401/12* (2013.01); *C07D 403/10* (2013.01); *C07D 403/12* (2013.01); *C07D 405/12* (2013.01); *C07D 413/12* (2013.01); *C07D 417/12* (2013.01); *C07D 417/14* (2013.01); *C07D 513/04* (2013.01); *G05B 19/418* (2013.01); *G05B 19/4189* (2013.01); *G05B 2219/31033* (2013.01);
(Continued)

(58) Field of Classification Search
CPC ......... H01L 21/67775; H01L 21/67769; H01L 21/67276; H01L 21/67772; H01L 21/67173; H01L 21/67161; H01L 21/67017; H01L 2924/00; Y10S 414/14; C07D 237/32; G01N 21/636; G01N 2021/646; G01N 2021/8825
See application file for complete search history.

(56) References Cited

U.S. PATENT DOCUMENTS 6,224,638 B1    5/2001  Jevtic et al.
6,351,686 B1 *  2/2002  Iwasaki ................. F02M 5/125
                                                700/121
(Continued)

FOREIGN PATENT DOCUMENTS

DE    10 2007 035 839 A1    2/2009
DE    10 2006 056 597 B4    3/2009
EP           1 626 011 B1    5/2009

OTHER PUBLICATIONS

Cao et al., Ga based approach for optimized scheduling in a semiconductor wafer fabrication, Jun. 2009, 4 pages.*
(Continued)

*Primary Examiner* — Thuy Dao
(74) *Attorney, Agent, or Firm* — Jones Day

(57) ABSTRACT

A method is provided. The method includes: assigning a buffer to a first wafer lot comprising a plurality of wafers according to a first trigger event associated with an equipment; and assigning a transporter to a second wafer lot comprising a plurality of wafers according to a second trigger event associated with the equipment.

18 Claims, 4 Drawing Sheets

```
┌─────────────────────────────────────────────────────┐
│ ASSIGN A BUFFER TO A FIRST WAFER LOT COMPRISING A   │
│ PLURALITY OF WAFERS ACCORDING TO A FIRST TRIGGER    │──702
│ EVENT ASSOCIATED WITH AN EQUIPMENT                  │
└─────────────────────────────────────────────────────┘
                          │
                          ▼
┌─────────────────────────────────────────────────────┐
│ ASSIGN A TRANSPORTER TO A SECOND WAFER LOT          │
│ COMPRISING A PLURALITY OF WAFERS ACCORDING TO A     │──704
│ SECOND TRIGGER EVENT ASSOCIATED WITH THE EQUIPMENT  │
└─────────────────────────────────────────────────────┘

700
```

(51) Int. Cl.
    *G01N 21/21*     (2006.01)
    *G01N 21/47*     (2006.01)
    *C07D 237/32*     (2006.01)
    *G05B 19/418*     (2006.01)
    *C07D 401/10*     (2006.01)
    *C07D 401/12*     (2006.01)
    *C07D 403/10*     (2006.01)
    *C07D 403/12*     (2006.01)
    *C07D 405/12*     (2006.01)
    *C07D 413/12*     (2006.01)
    *C07D 417/12*     (2006.01)
    *C07D 417/14*     (2006.01)
    *C07D 513/04*     (2006.01)
(52) U.S. Cl.
    CPC ..... *G05B 2219/32278* (2013.01); *Y02P 90/04* (2015.11); *Y02P 90/28* (2015.11)

(56) References Cited

U.S. PATENT DOCUMENTS

| | | | | |
|---|---|---|---|---|
| 6,470,231 B1* | 10/2002 | Yang | ..................... | G06Q 10/04 700/100 |
| 6,782,337 B2* | 8/2004 | Wack | ................... | G01N 21/211 250/559.24 |
| 6,946,394 B2* | 9/2005 | Fielden | ................ | G01N 21/211 257/E21.53 |
| 7,106,425 B1* | 9/2006 | Bultman | .............. | G01N 21/211 356/237.2 |
| 9,312,254 B2* | 4/2016 | Ken | ......................... | G03F 1/50 |
| 2010/0278622 A1* | 11/2010 | Huang | ................... | B66F 19/00 414/673 |
| 2013/0230375 A1 | 9/2013 | Tung et al. | | |
| 2016/0172312 A1* | 6/2016 | Nakamura | .............. | H01L 21/78 438/462 |

OTHER PUBLICATIONS

Klemmt et al., Scheduling jobs with time constraints between consecutive process steps in semiconductor manufacturing, Dec. 2012, 10 pages.*
Sobeyko et al., Genetic algorithms to solve a single machine multiple orders per job scheduling problem, Dec. 2010, 11 pages.*
German Office Action, Application No. 10 2014 019 164.8, dated Jun. 1, 2016.
Taiwan Office Action, Application No. 103146024, dated Jul. 29, 2016.

* cited by examiner

METHOD AND MANUFACTURING SYSTEM

FIELD

This disclosure relates generally to factories, and, more particularly, to a manufacturing system and method for manufacturing operations.

BACKGROUND

Usage rate of equipment in a factory refers to the ratio between effective work time and total time, and it is a key to improve throughput. Therefore, there is a need for increasing the usage rate or the effective work time.

SUMMARY

According to an exemplary embodiment of the disclosure, a manufacturing system is provided. The manufacturing system includes: a buffer, assigned to a first wafer lot according to a first trigger event associated with an equipment; a first transporter, assigned to a second wafer lot according to a second trigger event associated with the equipment; and a controller, using a real-time data associated with the equipment to assign the buffer to the first wafer lot and to assign the first transporter to the second wafer lot.

According to an exemplary embodiment of the disclosure, a method for manufacturing operation is provided. The method includes: assigning a buffer to a first wafer lot comprising a plurality of wafers according to a first trigger event associated with an equipment; and assigning a transporter to a second wafer lot comprising a plurality of wafers according to a second trigger event associated with the equipment.

According to an exemplary embodiment of the disclosure, a method for manufacturing operation is provided. The method includes: asking a first overhead hoist transport to prepare to transfer a first lot out of a tool after a current lot treatment to a current lot within the tool is complete; and asking a second overhead hoist transport to prepare to transfer a second lot to the tool after the current lot treatment within the tool is complete and the current lot is ready to move out of the tool.

DETAILED DESCRIPTION

Reference will now be made in detail to exemplary embodiments, which are illustrated in the accompanying drawings. Wherever possible, the same reference numbers will be used throughout the drawings to refer to the same or like parts.

Figure 1:
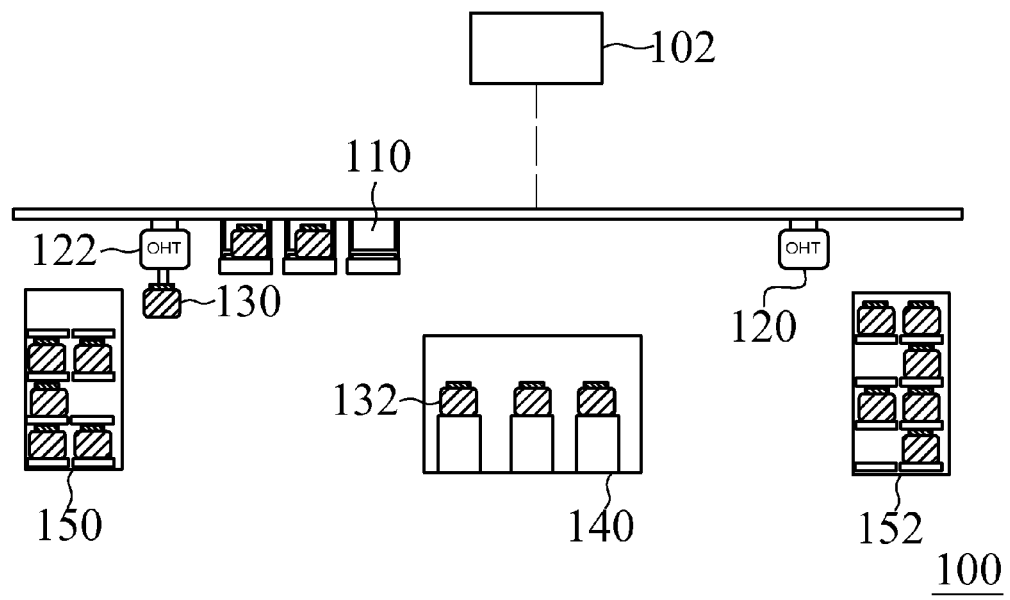
FIG. 1 is a schematic view illustrating an exemplary manufacturing system according to an exemplary embodiment of the disclosure.

FIG. 1 is a schematic view illustrating an exemplary manufacturing system according to an exemplary embodiment of the disclosure. As shown in FIG. 1, a manufacturing system 100 is provided. The manufacturing system 100 includes a buffer 110, a first transporter 120, and a controller 102. The buffer 110 is assigned to a first wafer lot 130 according to a first trigger event associated with equipment 140. The first transporter 120 is assigned to a second wafer lot 132 according to a second trigger event associated with the equipment 140. The controller 102 uses real-time data associated with the equipment 140 to assign the buffer 110 to the first wafer lot 130 and to assign the first transporter 120 to the second wafer lot 132. The buffer 110 may be, for example, a near tool buffer, an overhead buffer, a mini stocker, or an active load port. The first transporter 120 may be, for example, an overhead hoist transporter. The equipment 140 may include a plurality of chambers as processing units. And the equipment 140 may be, for example, a processing tool. The real-time data that the controller 102 uses may be, for example, an elapsed time or the remaining time that the equipment 140 has to start/finish a process at the present time instead of historical data from the past several months. The wafer lots 130, 132 may includes a plurality of wafers, such as twenty-five wafers in a lot.

Additionally, the controller 102 may assign the buffer 110 to the first wafer lot 130 according to the first trigger event associated with the equipment 140 instead of a priority value of the wafer lots. The controller 102 may assign the first transporter 120 to the second wafer lot 132 according to the second trigger event associated with the equipment 140, instead of having the second wafer lot 132 wait for the first transporter 120. As such, the assignment of buffer 110 and the first transporter 120 by the controller 102 may reduce usage rate loss of the equipment and wafer lot delivery time, as well as increasing the hit rate for delivering lots to the equipment and the full automation rate.

In the exemplary embodiment of FIG. 1, the manufacturing system 100 may further include a first stocker 150, a second stocker 152, and a second transporter 122. In the exemplary embodiment, the second transporter 122 moves the first wafer lot 130 from a first stocker 150 to the buffer 110 according to the first trigger event associated with the equipment 140. For example, the first trigger event associated with the equipment 140 may include whether the equipment 140 starts a process on a last wafer in the second wafer lot 132. The first trigger event associated with the equipment 140 may include whether a first remaining time that the equipment 140 starts a process on a last wafer in the second wafer lot 132 being less than a first period, for example, twenty minutes. The selection of the first wafer lot 130 may depend on the type of the second wafer lot 132 under processing in the equipment 140.

In another exemplary embodiment of FIG. 1, the controller 102 may asks the overhead hoist transport 120 to prepare to transfer the lot 132 out of the equipment 140 after a current lot treatment to a current lot within the equipment 140 is complete; and asking the overhead hoist transport 122 to prepare to transfer the lot 132 to the equipment 140 after the current lot treatment within the equipment 140 is complete and the current lot is ready to move out of the equipment 140. The current lot is not limited to lot 132 and may be any lot in the equipment 140.

Figure 2:
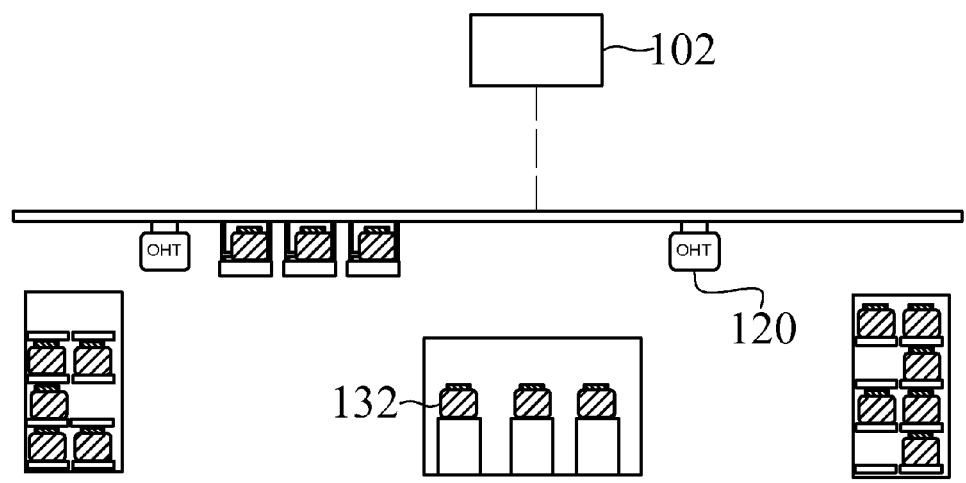
FIG. 2 is a schematic view illustrating an exemplary manufacturing system according to the exemplary embodiment of the disclosure.

FIG. 2 is a schematic view illustrating an exemplary manufacturing system according to the exemplary embodiment of the disclosure. As shown in FIG. 2, by the controller 102, the first transporter 120 shifts from a position far away from the equipment 140 to a position close to the equipment 140, and the first transporter 120 waits for the second wafer lot 132 according to the second trigger event associated with the equipment 140. For example, the second trigger event associated with the equipment 140 may include whether the equipment 140 finishes a process on a last wafer in the second wafer lot 132. The second trigger event associated with the equipment 140 may include whether a second remaining time that the equipment 140 needs to finish a process on a last wafer in the second wafer lot 132 is less than a second period, for example, twenty minutes.

Figure 3:
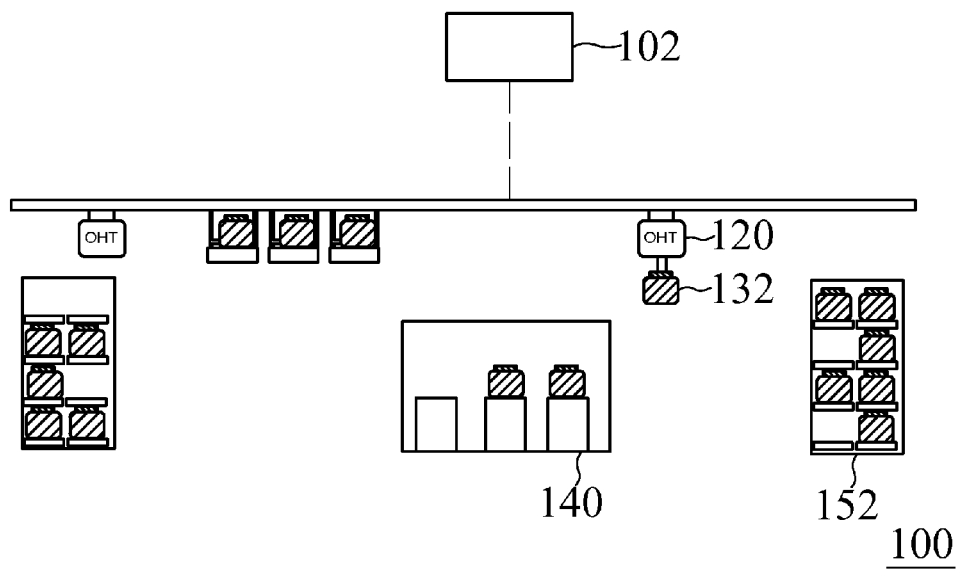
FIG. 3 is a schematic view illustrating an exemplary manufacturing system according to the exemplary embodiment of the disclosure.

FIG. 3 is a schematic view illustrating an exemplary manufacturing system according to the exemplary embodiment of the disclosure. As shown in FIG. 3, the first transporter 120 moves the second wafer lot 132 from the equipment 140 to the second stocker 152.

Figure 4:
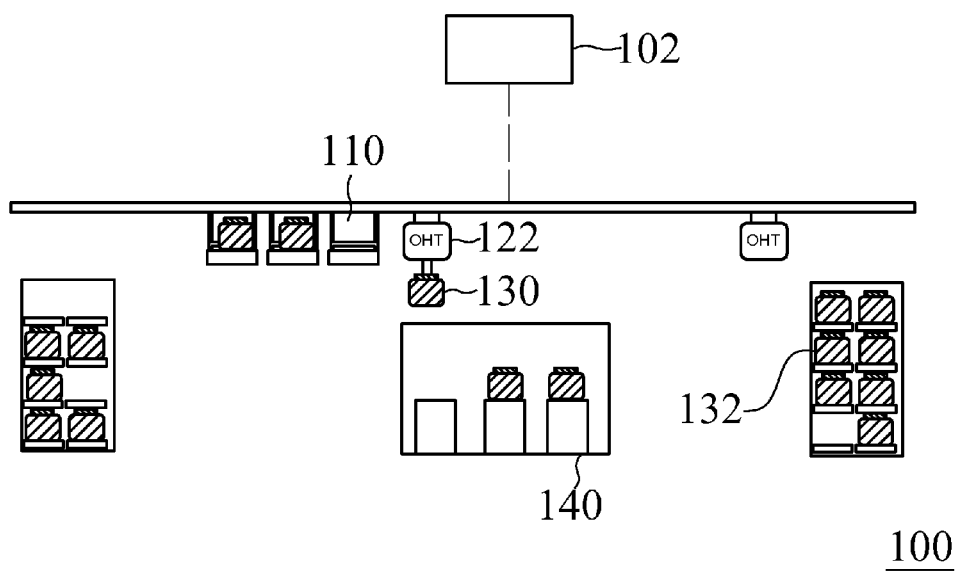
FIG. 4 is a schematic view illustrating an exemplary manufacturing system according to the exemplary embodiment of the disclosure.

FIG. 4 is a schematic view illustrating an exemplary manufacturing system according to the exemplary embodiment of the disclosure. As shown in FIG. 4, the second transporter 122 moves the first wafer lot 130 from the buffer 110 to the equipment 140.

Figure 5:
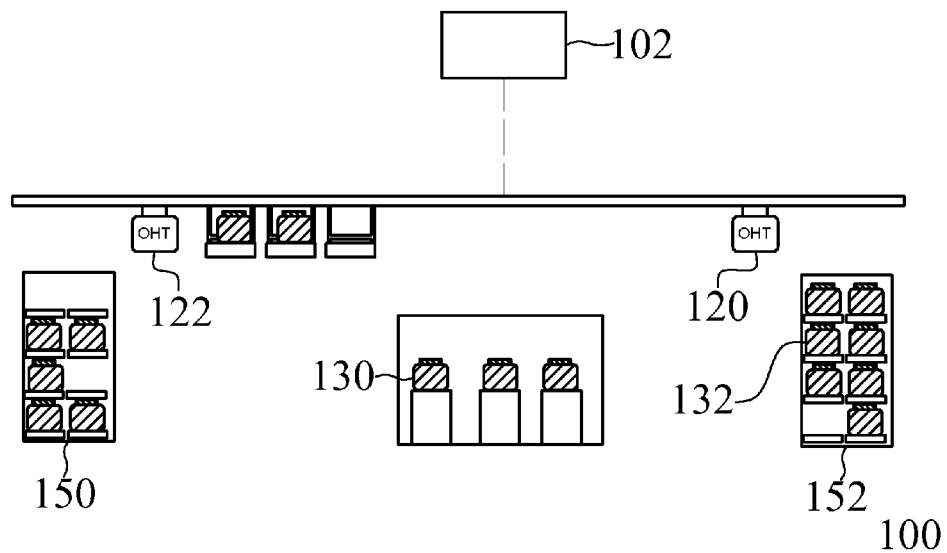
FIG. 5 is a schematic view illustrating an exemplary manufacturing system according to the exemplary embodiment of the disclosure.

FIG. 5 is a schematic view illustrating an exemplary manufacturing system according to the exemplary embodiment of the disclosure. As shown in FIG. 5, the first wafer lot 130 has been moved from the first stocker 150 to the equipment 140, and the second wafer lot 132 has been moved from the equipment 140 to the second stocker 152.

Figure 6:
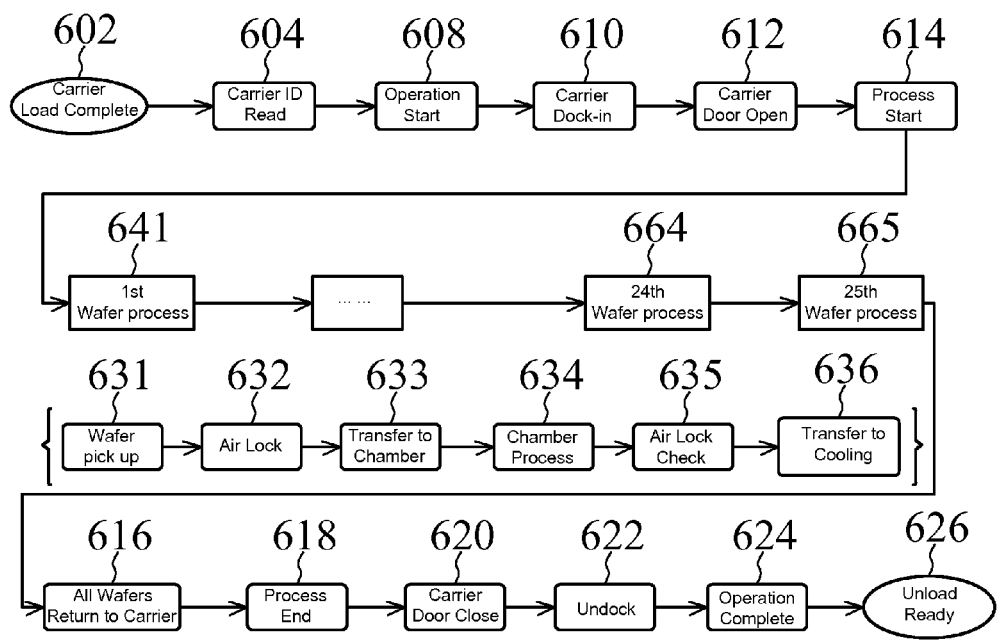
FIG. 6 is a flow chart illustrating an exemplary operation according to an exemplary embodiment of the disclosure.

FIG. 6 is a flow chart illustrating an exemplary operation according to an exemplary embodiment of the disclosure. As shown in FIG. 6, the operation 600 includes: carrier load complete (stage 602), carrier ID read (stage 604), start (stage 608), carrier dock-in (stage 610), carrier door open (stage 612), process start (stage 614), all wafers returning to carrier (stage 616), process end (stage 618), carrier door close (stage 620), undock (stage 622), completeness (stage 624), unload ready (stage 626), and wafer processes (stages 640-655). The stages 640-665 include wafer pick-up (stage 631), air lock (stage 632), transfer to chamber (stage 633), chamber process (stage 634), air lock check (stage 635), transfer to cooling (stage 636).

The first trigger event associated with the equipment 140 may be any event in the operation 600, for example, the stage 665 of the $25^{th}$ wafer processes. The second trigger event associated with the equipment 140 may be any event in the operation 600 as well, for example, the stage 616 of all wafers returning to carrier. Additionally, the first trigger event and the second trigger event may be whether a remaining time or an elapsed time that the equipment 140 starts or finished any event in the operation 600 is less than a time period. For example, the first trigger event may be whether a first remaining time that the equipment 140 starts the stage 665 of the $25^{th}$ wafer processes of the second wafer lot 132 is less than twenty minutes. The second trigger event may be whether a second remaining time that the stage 616 of all wafers of the second wafer lot 132 returning to carrier is less than twenty minutes. Examples of such events may be seen by reference to SEMI-E87/E93/E94, the disclosures of which are hereby incorporated by reference.

Figure 7:
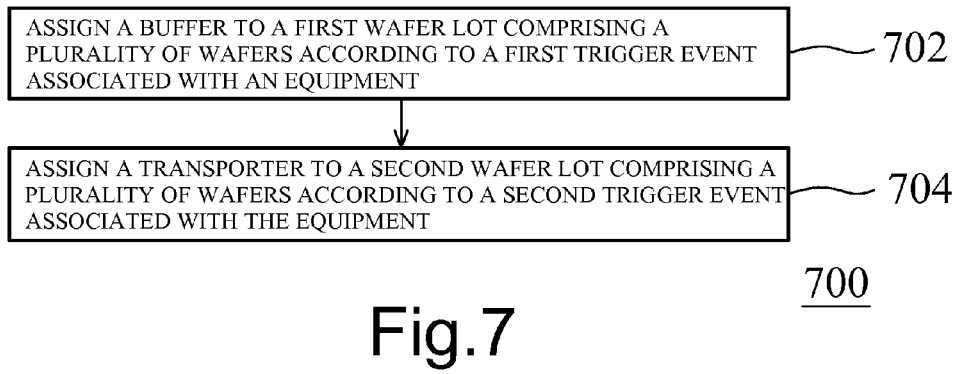
FIG. 7 is a flow chart for manufacturing operation according to an exemplary embodiment of the disclosure.

FIG. 7 is a flow chart for manufacturing operation according to an exemplary embodiment of the disclosure. As shown in FIG. 7, the method 700 includes the following operations: assigning a buffer to a first wafer lot comprising a plurality of wafers according to a first trigger event associated with an equipment (702); and assigning a transporter to a second wafer lot comprising a plurality of wafers according to a second trigger event associated with the equipment (704).

Figure 8:
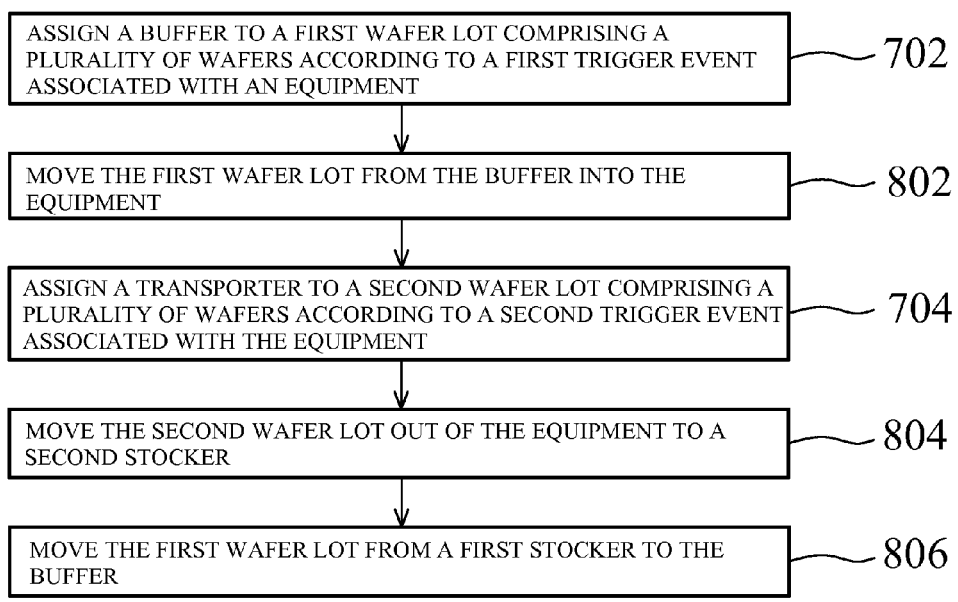
FIG. 8 is a flow chart for manufacturing operation according to an exemplary embodiment of the disclosure.

FIG. 8 is a flow chart for manufacturing operation according to an exemplary embodiment of the disclosure. As shown in FIG. 8, the method 800 includes the following operations: assigning a buffer to a first wafer lot comprising a plurality of wafers according to a first trigger event associated with an equipment (702); moving the first wafer lot from the buffer into the equipment (802); assigning a transporter to a second wafer lot comprising a plurality of wafers according to a second trigger event associated with the equipment (704); moving the second wafer lot out of the equipment to a second stocker (804); and moving the first wafer lot from a first stocker to the buffer (806).

In the exemplary embodiment, the operation of assigning the buffer to the first wafer lot according to the first trigger event associated with the equipment may include: assigning the buffer to the first wafer lot according to whether the equipment starts a process on a last wafer in the second wafer lot; and when the equipment starts the process on the last wafer in the second wafer lot, moving the first wafer lot to the buffer.

In the exemplary embodiment, the operation of assigning the buffer to the first wafer lot according to the first trigger event associated with the equipment may include: assigning the buffer to the first wafer lot according to whether a first remaining time that the equipment starts a process on a last wafer in the second wafer lot is less than a first period; and when the first remaining time is less than the first period, moving the first wafer lot to the buffer.

In the exemplary embodiment, the operation of assigning the transporter to the second wafer lot according to the second trigger event associated with the equipment may include: assigning the transporter to the second wafer lot according to whether the equipment finishes a process on a last wafer in the second wafer lot; and when equipment finishes the process on the last wafer in the second wafer lot, moving the transporter to wait for the second wafer lot.

In the exemplary embodiment, the operation of assigning the transporter to the second wafer lot according to the second trigger event associated with the equipment may include: assigning the transporter to the second wafer lot according to whether a second remaining time that the equipment needs finishing a process on a last wafer in the second wafer lot is less than a second period; and when the second remaining time is less than the second period, moving the transporter to wait for the second wafer lot.

This written description uses examples to disclose the disclosure, include the best mode, and also to enable a person skilled in the art to make and use the disclosure. The patentable scope of the disclosure may include other examples that occur to those skilled in the art.

One skilled in the relevant art will recognize that the various embodiments may be practiced without one or more of the specific details, or with other replacement and/or additional methods, materials, or components. Well-known structures, materials, or operations may not be shown or described in detail to avoid obscuring aspects of various embodiments of the disclosure. Various embodiments shown in the figures are illustrative example representations and are not necessarily drawn to scale. Particular features, structures, materials, or characteristics may be combined in any suitable manner in one or more embodiments. Various additional layers and/or structures may be included and/or described features may be omitted in other embodiments. Various operations may be described as multiple discrete operations in turn, in a manner that is most helpful in understanding the disclosure. However, the order of description should not be construed as to imply that these operations are necessarily order dependent. In particular, these operations need not be performed in the order of presentation. Operations described herein may be performed in a different order, in series or in parallel, than the described embodiment. Various additional operations may be performed and/or described. Operations may be omitted in additional embodiments.

This written description and the following claims may include terms, such as left, right, top, bottom, over, under, upper, lower, first, second, etc. that are used for descriptive purposes only and are not to be construed as limiting. For example, terms designating relative vertical position may refer to a situation where a device side (or active surface) of a substrate or integrated circuit is the "top" surface of that substrate; the substrate may actually be in any orientation so that a "top" side of a substrate may be lower than the "bottom" side in a standard terrestrial frame of reference and may still fall within the meaning of the term "top." The term "on" as used herein (including in the claims) may not indicate that a first layer "on" a second layer is directly on and in immediate contact with the second layer unless such is specifically stated; there may be a third layer or other structure between the first layer and the second layer on the first layer. The embodiments of a device or article described herein may be manufactured, used, or shipped in a number of positions and orientations. Persons skilled in the art will recognize various equivalent combinations and substitutions for various components shown in the figures.

What is claimed is:

1. A method performed by a controller of a wafer-manufacturing system, the method comprising:
   receiving real-time data associated with processing, by a tool, a second wafer lot having at least two wafers that is in the tool;
   in response to a trigger event, causing a first transporter to transport a first wafer lot from a first stocker to a buffer; and
   in response to completion of the processing of the second wafer lot:
      causing a second transporter to transfer the second wafer lot out of the tool, and
      causing the first transporter to transfer the first wafer lot from the buffer to the tool;
   wherein the trigger event is a first predetermined amount of time before the tool will start to process the last wafer in the second wafer lot, and
   at a second predetermined amount of time before the completion of the processing of the second wafer lot, causing the second transporter to move to a position close to the tool to wait for the second wafer lot, wherein the first predetermined amount of time is different from the second predetermined amount of time.

2. The method of claim 1, wherein the trigger event is the tool starting to process a last wafer in the second wafer lot.

3. The method of claim 1, wherein the trigger event is a predetermined amount of time before the tool will start to process the last wafer in the second wafer lot.

4. The method of claim 1, wherein the causing of the second transporter to transfer the second wafer lot out of the tool includes causing the second transporter to transfer the second wafer lot to a second stocker.

5. The method of claim 1, wherein the predetermined amount of time is a first predetermined amount of time, and wherein the method further comprises:
   at a second predetermined amount of time before the completion of the processing of the second wafer lot, causing the second transporter to move to a position close to the tool to wait for the second wafer lot.

6. The method of claim 1, wherein each of the first and second transporters comprises an overhead hoist transporter, and the buffer comprises a near tool buffer, an overhead buffer, a mini stocker, or an active load port.

7. A method performed by a wafer-manufacturing system, the method comprising:
   processing, by a tool, a second wafer lot that is in the tool;
   in response to a trigger event, transferring by a first transporter a first wafer lot having at least two wafers from a first stocker to a buffer; and
   in response to completion of the processing of the second wafer lot:
      transferring, by a second transporter, the second wafer lot out of the tool; and
      transferring, by the first transporter, the first wafer lot from the buffer to the tool;
   wherein the trigger event is a first predetermined amount of time before the tool will start to process the last wafer in the second wafer lot; and
   at a second predetermined amount of time before the completion of the processing of the second wafer lot, the second transporter moving to a position close to the tool to wait for the second wafer lot, wherein the first predetermined amount of time is different from the second predetermined amount of time.

8. The method of claim 7, wherein the trigger event is the tool starting to process a last wafer in the second wafer lot.

9. The method of claim 7, wherein the trigger event is a predetermined amount of time before the tool will start to process the last wafer in the second wafer lot.

10. The method of claim 7, wherein the second transporter transferring the second wafer lot out of the tool includes the second transporter to transferring the second wafer lot to a second stocker.

11. The method of claim 7, wherein the predetermined amount of time is a first predetermined amount of time, and wherein the method further comprises:
    at a second predetermined amount of time before the completion of the processing of the second wafer lot, moving the second transporter to a position close to the tool to wait for the second wafer lot.

12. The method of claim 7, wherein each of the first and second transporters comprises an overhead hoist transporter, and the buffer comprises a near tool buffer, an overhead buffer, a mini stocker, or an active load port.

13. A manufacturing system comprising:
    a tool configured to process a second wafer lot having at least two wafers that is in the tool;
    a buffer;
    a first transporter;
    a second transporter; and
    a controller configured to:
       in response to a trigger event, cause the first transporter to transport a first wafer lot from a first stocker to a buffer; and in response to completion of the processing of the second wafer lot,
  (i) cause the second transporter to transfer the second wafer lot out of the tool, and
  (ii) cause the first transporter to transfer the first wafer lot from the buffer to the tool; wherein the trigger event is a first predetermined amount of time before the tool will start to process the last wafer in the second wafer lot; and
at a second predetermined amount of time before the completion of the processing of the second wafer lot, cause the second transporter to move to a position close to the tool to wait for the second wafer lot, wherein the first predetermined amount of time is different from the second predetermined amount of time.

14. The system of claim 13, wherein the trigger event is the tool starting to process a last wafer in the second wafer lot.

15. The system of claim 13, wherein the trigger event is a predetermined amount of time before the tool will start to process the last wafer in the second wafer lot.

16. The system of claim 13, wherein the second transporter transferring the second wafer lot out of the tool includes the second transporter transferring the second wafer lot to a second stocker.

17. The system of claim 13, wherein the predetermined amount of time is a first predetermined amount of time, and wherein the controller is configured to, at a second predetermined amount of time before the completion of the processing of the second wafer lot, cause the second transporter to move to a position close to the tool to wait for the second wafer lot.

18. The system of claim 13, wherein each of the first and second transporters comprises an overhead hoist transporter, and the buffer comprises a near tool buffer, an overhead buffer, a mini stocker, or an active load port.

* * * * *